United States Patent [19]

Reck et al.

[11] Patent Number: 4,473,909
[45] Date of Patent: Oct. 2, 1984

[54] AUDITORY OSSICLE PHOSTHESIS

[75] Inventors: Ralf Reck, Mainz-Bretzenheim; Heinz Broemer, Hermannstein; Klaüs-Konrad Deutscher, Wetzlar, all of Fed. Rep. of Germany

[73] Assignee: Ernst Leitz Wetzlar GmbH, Wetzlar, Fed. Rep. of Germany

[21] Appl. No.: 385,371

[22] PCT Filed: Oct. 1, 1980

[86] PCT No.: PCT/DE80/00141
§ 371 Date: May 26, 1982
§ 102(e) Date: May 26, 1982

[87] PCT Pub. No.: WO82/01127
PCT Pub. Date: Apr. 15, 1982

[30] Foreign Application Priority Data

Sep. 26, 1980 [DE] Fed. Rep. of Germany ....... 3036245

[51] Int. Cl.³ .............................................. A61F 1/00
[52] U.S. Cl. .............................................. 3/1; 3/1.9; 128/92 C
[58] Field of Search ................... 3/1, 1.9; 128/1, 92 C, 128/334

[56] References Cited

U.S. PATENT DOCUMENTS 4,287,616 9/1981 Heimke .................................... 3/1.9

OTHER PUBLICATIONS

Reck, R. Archiv fur Ohren-, Nasen- und Kehlkopfheilkunde, "Archives of Oto-Rhino-Laryngology", vol. 223, Nos. 2-4, 1979, pp. 369-372.

Primary Examiner—Richard J. Apley
Assistant Examiner—David J. Isabella
Attorney, Agent, or Firm—Schwartz, Jeffery, Schwaab, Mack, Blumenthal & Koch

[57] ABSTRACT

An auditory ossicle prosthesis is described, comprising a plate (1), a shaft (2) applied eccentrically to the underside (3) of the plate and a groove (7) set into the top side (8) of the plate. The plate (1) has a mirror symmetric configuration with respect to at least one symmetry plane (5) perpendicular to the plane of the plate (8). The shaft (2) is applied so that its contact surface (4) is located on the trace (5) of the (principal) symmetry plane (5) of the plate (1), but at least removed from the boundary area of the plate (1) by one half of the shaft cross section. Preferably, the axis (9) of the shaft (2) includes with the normal (10) of the underside (3) of the plate an angle $\alpha$ of the order of magnitude of $\alpha = 15° \pm 5°$. The groove (7) is arranged in the top side (8) of the plate, in its front half and aligned perpendicularly to the symmetry plane (5) of the prosthesis. The prosthesis may consist of a single piece or of two pieces. It consists of a bioactive material.

A process is further provided for the final treatment of the prosthesis immediately prior to or during the implantation process. This process is characterized in that a bioactive powder material, in particular homologous bone particles, is sprinkled onto the prosthesis which has been prepared for implantation. This may also be effected during the actual implantation process in situ.

24 Claims, 10 Drawing Figures

AUDITORY OSSICLE PHOSTHESIS

BACKGROUND OF THE INVENTION

The application concerns an auditory ossicle prosthesis consisting of a bioactive material and a process for its final treatment immediately prior to and during the implantation process.

For the complete or partial reconstruction of the auditory ossicle chain, implants of various material are used. Recently, synthetic plastic materials have acquired a certain importance, because of their relatively low specific gravity and ready workability also in the intraoperative phase of the adaptation of industrially performed implants to individual conditions. In spite of the low reactivity of the implant support and the inertness of the synthetic materials, the long term success of these implants in the middle ear is not assured, as with time they penetrate the tympanic membrane.

From DE-OS No. 2 905 183 a single piece auditory ossicle prosthesis of a bioinert $Al_2O_3$ material is known; it consists of a circular plane parallel plate with a center symmetrical straight shaft or an oblique shaft engaging eccentrically on the under side of the plate in its peripheral area, with an angle of inclination of approximately 30° with respect to the normal to the plate. This known prosthesis has at least one groove in the top side of the plate, wherein if only one groove is present, the latter traverses the surface of the plate in a center symmetrical manner and if two or three parallel grooves are present, they are arranged with mirror symmetry on the circular top side of the plate. It is an essential characteristic of DE-OS No. 2 905 183 that the groove or grooves in the inclined shaft prosthesis are parallel to the plane, defined by the normal to the plate and the shaft axis.

The bioinert aluminum oxide material used induces only slight reactions in the bone tissue—wherein the thickness of the separating connective tissue layer formed may be considered a measure of biocompatibility—but as the $Al_2O_3$ material is present in a completely inert state in the area of the middle ear, limitations concerning its long term success similar to those of the abovementioned synthetic materials must be accepted.

From "Archiv fur Ohren-, Nasen- und Kehlkopfheilkunde, Archives of Oto-Rhino-Laryngolgy", Vol. 223, No. 2-4, 1979, pp. 369-372, tympanoplastics consisting of bioactive glass ceramics are further known; they are surrounded in vivo by a 40 μm thick bone layer. The configuration of the prosthessis disclosed corresponds to an excentric straight shaft arrangement, with the top side of the plate consisting of a nonplanar, spherical or ellipsoidal surface, without groove like notches.

It has been found that the implant configurations known heretofore have the disadvantage that they are not adaptable in an optimal manner to the complex middle ear anatomy and that in view of the special local conditions, they cannot be maintained stable for a long period of time. In the case of the groove orientation parallel to the plane of symmetry of an oblique shaft prosthesis known from DE-OS No. 2 905 183, there is the long term risk that in a patient exposed to unexpected strong jarring pulses particularly in the vertical direction of the human body—such as may occur during jumping, the climbing of stairs or especially during accidents, etc.—the prosthesis implanted may be "shaken" from its purely mechanical anchoring.

A further disadvantage found in the meantime consists of the fact that in many cases the surface of the plate surface has a spherical cap like configuration, leading to exposure to a nonuniform and locally strongly enhanced pressure application upon contact with the tympanic membrane. Furthermore, a groove, possibly milled in subsequently, especially when not cut center symmetrically into the lens shaped top side of the plate, offers only a relatively slight mechanical hold for the auditory meatus of the body itself, engaging said groove.

SUMMARY OF THE INVENTION

It is therefore the object of the invention to provide auditory ossicle prostheses optimally adapted or adaptable to the local anatomy, upon which—with respect to their spatial configuration in individual cases slight mechanical alterations must be effected, for example a correction of the length of the shaft, and which—as far as the material of the prosthesis is concerned—by virtue of its special finish treatment cause the development of a lamellar covering of a thickness of several layers of cells, on the surface of the prosthesis in vivo.

This object is attained in the case of an auditory ossicle prosthesis of the aforementioned type according to the invention in that the plate has a mirror symmetrical configuration with respect to at least one symmetry plane perpendicular to the plane of the plate, that the shaft is applied to the rear half of the underside of the plate so that its contact surface is located on the intersection line of the (principal) symmetry plane with the plate, but removed at least by one half of the diameter of the shaft cross section from the edge of the plate, that the groove is arranged on the top side of the plate in its front half and aligned perpendicularly to the symmetry plane of the prosthesis and that the prosthesis consists of a bioactive material.

It is appropriate for the plate to have a rectangular configuration and be arranged so that the longer side of the rectangle is parallel to the symmetry plane of the prosthesis. It is also possible for the plate to have an ellipsoidal configuration and be arranged so that the longer axis of the ellipsoid is coincidental with the intersection line of the symmetry plane of the prosthesis.

The configuration of the plate may further be such that it has only one symmetry plane perpendicular to it and that said symmetry plane coincides with the intersection line of the symmetry plane of the prosthesis. The edges of the top side of the plate and the corners of the plates may advantageously be rounded. It is also possible for the thickness of the plate to continuously decrease or increase toward its front half. According to a preferred form of embodiment, the axis of the shaft includes an angle $\alpha$ of the order of magnitude of $\alpha = 15° \pm 5°$ with the normal of the bottom side of the plate. It may be appropriate to have a circular or ellipsoidal configuration of the cross section of the shaft. A shape of the shaft continuously narrowing from the contact surface of the shaft on the bottom side of the plate to its end may be advantageous. Conveniently, the cross section of the groove is semicircular or triangular with a rounded apex. It is further possible that the edges formed by the groove with the top side of the plate are not parallel.

The configuration of the groove in the top side of the plate may further be such that the edges formed by the groove with the top side of the plate are rounded. Advantageously, the depth of the groove corresponds at the most to one-half of the thickness of the plate at its front edge and the distance between the front edge of the top side of the plate and the first edge of the groove is at least equal to one-half of the width of the groove.

According to a preferred embodiment, the prosthesis consists of a bioactive composite material, for example, one based on methylmethacrylate with dispersions of embedded bioactive particles or of an apatite containing sinter product, or of a bioactive glass ceramic or a bioglass.

It is further possible in principle to provide the prosthesis not in one but in two pieces, consisting of a plate and a shaft part. It is particularly advantageous to equip the surface of the prosthesis additionally with a coating layer consisting of a bioactive material in the powder form. It has been found to be appropriate to have this layer consist of homologous bone particles, for example, bone chips or powders. A final finishing of the prosthesis is characterized in that the coating layer in powder form is applied immediately prior to the implantation process itself, in situ, by sprinkling the powder onto the prosthesis.

The advantages of the auditory ossicle prosthesis according to the invention primarily consist of the fact that due to the fundamentally different orientation of the relative position of the groove on the top side of the plate in combination with the anatomically correct angling of the oblique shaft and the detailed geometrical configuration of the entire prosthesis, mainly, however, because of the selection of the prosthesis material, for the first time a permanent prosthesis with outstanding local, anatomically correct placement stability, excellent miro-lever action for the functionally correct transmission of vibrations, with universal applicability in restorative surgery of the area of the middle ear, with mechanically very simple "trimmability" to individual anatomical requirements, together with excellent properties in the complex auditory ossicle chain, may be provided.

BRIEF DESCRIPTION OF THE DRAWINGS

In the drawings, exemplary embodiments of the invention are schematically represented. The drawings show

DETAILED DESCRIPTION OF PREFERRED EMBODIMENTS

Figure 1:
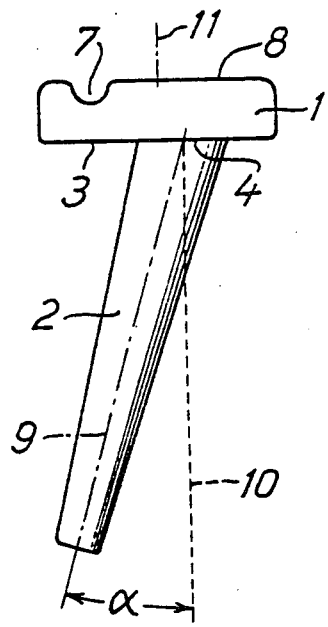
FIG. 1: a first embodiment of the prosthesis according to the invention (oblique shaft prosthesis) in a lateral elevation.

In FIG. 1, a plane parallel plate 1 has a shaft circular in its cross section applied to it, with the axis 9 of said shaft forming with the normal 10 to the underside of the plate 3 an angle $\alpha$, which within an angular range of $10° \leq \alpha \leq 20°$ may assume any value.

Figure 2:
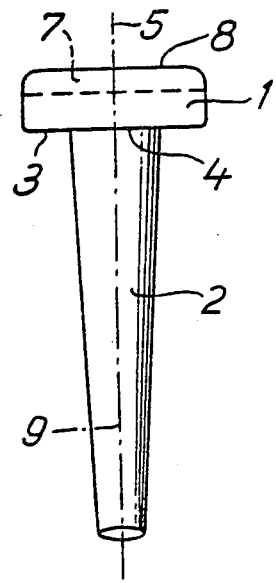
FIG. 2: a front elevation of the prosthesis shown in FIG. 1.
Figure 3:
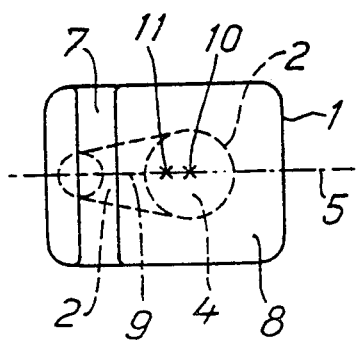
FIG. 3: a top view of the prosthesis of FIG. 1.
Figure 4:
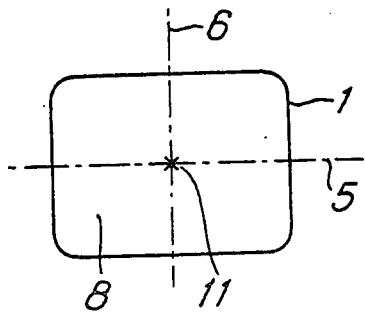
FIG. 4: the symmetry conditions of the prosthesis plate shown in FIG. 1.

As seen in FIGS. 1 and 2, the shaft 2 narrows continuously from the underside of the plate 3 to its end. The plate 1 has a rectangular configuration with rounded corners and edges. It has a principal symmetry plane perpendicular to the plane of the drawing, the intersection line 5 of which is shown in FIGS. 2–4. A secondary symmetry plane is perpendicular to the plane of the drawing and the principal symmetry plane of the plate; observe the intersection line 6 shown in FIG. 4. The intersection of the lines 5 and 6 of the aforementioned symmetry planes is the geometrical center 11 of the plate. The intersection line 5 of the principal symmetry plane of the plate 1 and the axis 9 of the shaft 2 define a plane designated the prosthesis symmetry plane. By definition, its trace coincides with the line 5.

FIG. 3 indicates that the contact surface 4 of the shaft 2 and the point of impact of the shaft axis 9 on the underside 3 of the plate do not coincide with the center of the plate. Rather, the shaft is eccentric to the plate and is applied to the rear part of it. In the present application, the mentioning and graphical representation of a "contact surface 4" and the mentioning of the eccentric "application" of the shaft to the plate underside 3, merely serve the purpose of a detailed, orderly explanation of the spatial configuration according to the invention. The prosthesis may consist of two individual pieces, namely a plate 1 and a shaft 2, but it may also consist of a single unit.

A groove 7 is located on the top side 8 of the plate, perpendicularly to the symmetry plane of the prosthesis. It is located in the front part of the top side 8 of the plate. The groove 7 is also located eccentrically with respect to the center 11 of the plate and the secondary symmetry plane 6, respectively. It is essential that the groove be perpendicular to the symmetry plane of the prosthesis, because in this manner the optimum, positive engagement of existing middle ear fragments and thus the long term positioning without tilting of the implant, is assured.

Figure 5:
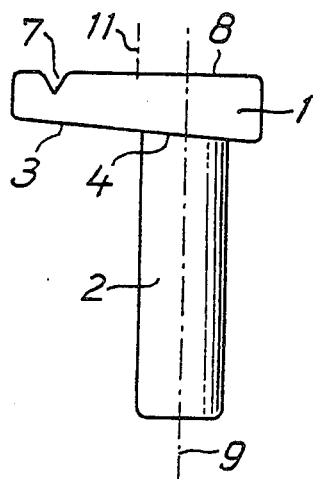
FIG. 5: a second embodiment of the prosthesis according to the invention (straight shaft prosthesis) in a lateral elevation.
Figure 6:
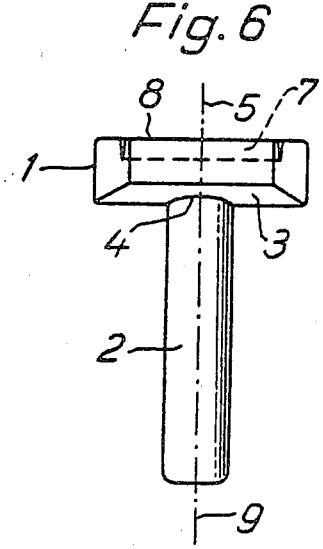
FIG. 6: a front view of the prosthesis shown in FIG. 5.
Figure 7:
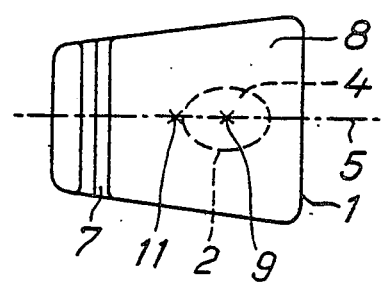
FIG. 7: a top view of the prosthesis shown in FIG. 5.

In FIGS. 5–7, another embodiment of the invention is shown in three different views. The plate 1 has a flat underside 3 and a flat top side 8, but the thickness of the plate increases continuously from the front to the rear.

The axis 9 of the shaft 2 includes a small angle with the normal to the underside 3 of the plate in this case, corresponding to the inclination of the underside 3 with respect to the horizontal top side 8; however, the form of embodiment shown in FIG. 5 and 6 still represents a "straight shaft prosthesis", since the angle between the top side 8 of the plate and the axis 9 of the shaft is a right angle. The shaft has an elliptical cross section, with the principal axis of the elliptical contact surface 4 being located in the intersection line 5 of the symmetry plane of the prosthesis. It is naturally also possible to narrow the elliptical cross section of the shaft continuously toward its end, as shown in the first examplary embodiment. It is further within the scope of the invention to selectively flatten the shaft along its circumference, when needed. Similarly, the plate thickness may be larger in the front area than in the rear. It is further possible to adapt the geometry of the groove cross section selectively to individual requirements; compare FIGS. 1 and 5.

The blunting or rounding of all of the edges and corners of the prosthesis, particularly on the top side 8 of the plate, is absolutely necessary because of the enormous danger of perforation or penetration in the area of the tympanic membrane.

The plate 1 has in FIG. 7 the form of a double trapezoid. However, it is also possible to provide other configurations with only one symmetry plane 5, as shown approximately in FIG. 9 (in the shape of a bow of a ship) and in FIG. 10 (pear shape) in individual cases or to mill such shapes from a prosthesis having a rectangular plate.

Figure 8:
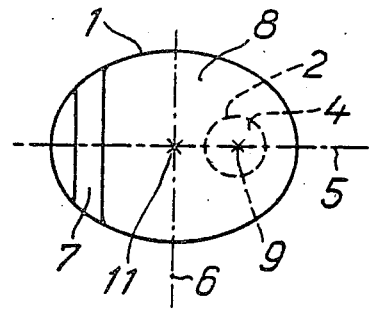
FIG. 8: a third, doubly symmetrical embodiment of the prosthesis plate.

A form with a higher degree of symmetry having principal and secondary symmetry planes 5 and 6 is shown in FIG. 8 (elliptical).

In all of these cases the groove 7 is essentially perpendicular to the symmetry plane 5 of the prosthesis.

Figure 9:
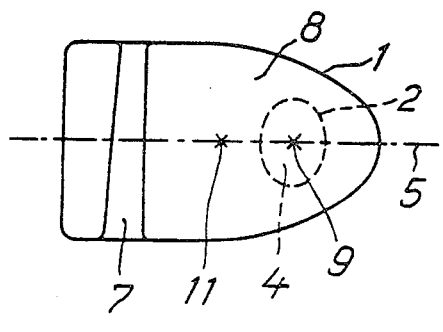
FIG. 9: a fourth, single symmetrical embodiment of the prosthesis plate.
Figure 10:
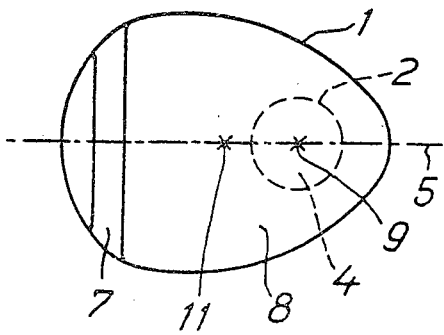
FIG. 10: a fifth, single symmetrical embodiment of the prosthesis plate.

In FIG. 9 a form of the groove on the top side 8 of the plate is shown with nonparallel edges. It can contribute to an additional wedging and thus to a higher degree of mechanical clamping.

The following essential spatial characteristics are common to all of the detail solutions proposed: the configuration of the plate is symmetrical at least with respect to the symmetry plane 5 of the entire prosthesis; the contact surface 4 of the shaft 2 is always eccentric with respect to the center 11 of the plate and is always located on the intersection line 5 of the symmetry plane of the prosthesis, without, however, arriving in the immediate boundary area of the rear part of the underside 3 of the plate; the groove is at least with one of its edges always perpendicular to the symmetry plane 5 of the plate or to the entire prosthesis and is eccentric with respect to the center 11 of the plate, without itself arriving in the immediate boundary area of the front part of the top side 8 of the plate.

This configuration results in an optimum micro-lever action, which together with a mechanically stable overall design and the anatomically accurate location of the implant, are decisive for the superior properties of the prosthesis according to the invention.

The positive overall effect of this novel prosthesis configuration is further enhanced in numerous applications by the choice of known bioactive materials as the material of the prosthesis. Even though the fixed bond between the implant and a bone obtainable in principle with this material, such as that absolutely required for bone and articulated joint replacements, is not used in this instance, the bioactive property has been found to be particularly appropriate in this special area of prosthetic surgery. Although the bio-material is not osteoinductive, i.e., not primarily bone forming, an existing bone tissue in the immediate vicinity of the implant may grow onto the bio-substance in the form of lamella of a thickness of three to four cell layers, thereby covering the implant.

A surgeon intending to implant the auditory ossicle prosthesis may dust it immediately prior to the implantation in vitro with very fine bone particles originating with the patient (homologous), or the prosthesis already insitu may be covered in the course of the implantation with a very fine bone powder, obtained during minor bone wall corrections or other mini-milling, boring or grinding work in the area of the middle ear. It has been found surprisingly in clinical testing that in the case of auditory ossicles loosely covered in this manner, a lamellar covering is formed on their surface, in vivo, in the course of a kinetic formation process of several weeks.

It has thus been ascertained that this formation process is causally related to the bioactive prosthesis material chosen.

We claim:

1. An auditory ossicle prosthesis, comprising: a generally planar plate; a shaft attached eccentrically to the underside of said plate; and a groove provided in the top side of the plate, wherein
    (a) the plate and attached shaft have a mirror symmetrical configuration with respect to at least one symmetry plane perpendicular to the plane of the plate and passing through the shaft;
    (b) the shaft is attached so that its contact surface with the plate is located on the symmetry plane of the plate, but is removed by at least one-half of the diameter of the shaft from the boundary area of the plate;
    (c) the groove is arranged on the top side of the plate in its front half and is aligned perpendicularly to the symmetry plane of the prosthesis; and
    (d) the prosthesis is comprised of a bioactive material.

2. An auditory ossicle prosthesis according to claim 1, wherein the plate has a generally rectangular shape and is arranged so that the longer side of the rectangle is parallel to the symmetry plane of the prosthesis.

3. An auditory ossicle prosthesis according to claim 1, wherein the plate has the configuration of an ellipsis and is arranged so that the longer axis of the ellipsis coincides with the symmetry plane of the prosthesis.

4. An auditory ossicle prosthesis according to claim 1, wherein the plate has a single symmetry plane perpendicular to it and said symmetry plane coincides with the symmetry plane of the prosthesis.

5. An auditory ossicle prosthesis according to claim 1, wherein the edges of the top side and the corners of the plate are generally rounded.

6. An auditory ossicle prosthesis according to claim 1, wherein the thickness of the plate increases continuously toward its front half.

7. An auditory ossicle prosthesis according to claim 1, wherein the thickness of the plate continuously increases toward its rear half.

8. An auditory ossicle prosthesis according to claim 1, wherein the axis of the shaft is inclined at an angle of approximately $15°\pm5°$ with respect to the normal to the underside of the plate.

9. An auditory ossicle prosthesis according to claim 1, wherein the cross section of the shaft is circular.

10. An auditory ossicle prosthesis according to claim 1, wherein the cross section of the shaft is ellipsoidal.

11. An auditory ossicle prosthesis according to claim 1, wherein the shaft continuously narrows from its contact surface on the underside of the plate to the distal end of the shaft.

12. An auditory ossicle prosthesis according to claim 1, wherein the cross section of the groove is substantially semicircular.

13. An auditory ossicle prosthesis according to claim 1, wherein the cross section of the groove has the configuration of a triangle with a round apex.

14. An auditory ossicle prosthesis according to claim 1, wherein the edges formed by the groove with the top side of the plate are not parallel.

15. An auditory ossicle prosthesis according to claim 1, wherein the edges formed by the groove with the top side of the plate are rounded.

16. An auditory ossicle prosthesis according to claim 1, wherein the depth of the groove is at the most one half of the thickness of the plate at its front edge.

17. An auditory ossicle prosthesis according to claim 1, wherein the distance between the front edge of the top side and the first edge of the groove closest to said front edge is at least one half of the width of the groove.

18. An auditory ossicle prosthesis according to claim 1, wherein the bioactive material is a composite.

19. An auditory ossicle prosthesis according to claim 1, wherein the bioactive material comprises an apatite-containing sintered product.

20. An auditory ossicle prosthesis according to claim 1, wherein the bioactive material comprises glass ceramic.

21. An auditory ossicle prosthesis according to claim 1, wherein the bioactive material comprises a bioglass.

22. An auditory ossicle prosthesis according to claim 1, wherein the prosthesis is comprised of two individual parts attached together.

23. An auditory ossicle prosthesis according to claim 1, further comprising a supplemental covering layer on its surface, said layer comprising a bioactive material in powder form.

24. An auditory ossicle prosthesis according to claim 23, wherein the covering layer comprises autologous or homologous bone particles.

* * * * *